United States Patent [19]

Lieberman

[11] Patent Number: 4,512,039
[45] Date of Patent: Apr. 23, 1985

[54] METHOD OF OFFSETTING POSTOPERATIVE ASTIGMATISM WITH AN INTRAOCULAR LENS

[76] Inventor: David M. Lieberman, 9 Prospect Park West, Brooklyn, N.Y. 11215

[21] Appl. No.: 497,504

[22] Filed: May 24, 1983

[51] Int. Cl.³ ............................ A61F 1/16; A61F 1/24
[52] U.S. Cl. ................................................................ 3/13
[58] Field of Search .......................................... 3/13, 1

[56] References Cited

U.S. PATENT DOCUMENTS

| | | |
|---|---|---|
| 4,092,743 | 6/1978 | Kelman ........................................ 3/13 |
| 4,254,510 | 3/1981 | Tennant ....................................... 3/13 |
| 4,277,852 | 7/1981 | Poler ............................................. 3/13 |
| 4,315,336 | 2/1982 | Poler ............................................. 3/13 |
| 4,361,913 | 12/1972 | Streck .......................................... 3/13 |

OTHER PUBLICATIONS

Lens Implantation (book), by P. Leonard & J. Rommel, Dr. W. Junk Publishers, The Hague-Boston-London, 1982, pp. 136-137.

Primary Examiner—Ronald L. Frinks
Attorney, Agent, or Firm—Anthony J. Casella; Gerald E. Hespos

[57] ABSTRACT

A toric intraocular lens is provided to eliminate or substantially reduce the expected postoperative astigmatism induced by eye surgery. The lens is constructed such that the finally placed vertical meridian is optically weaker than the horizontal meridian. The lens is constructed to ensure that the vertical meridian will be properly aligned when placed in the eye, such as by disposing the haptics along the vertical meridian.

3 Claims, 6 Drawing Figures

METHOD OF OFFSETTING POSTOPERATIVE ASTIGMATISM WITH AN INTRAOCULAR LENS

BACKGROUND OF THE INVENTION

The lens of the human eye is located centrally behind the pupil and is protected by the cornea. In the normal eye, the lens is clear and substantially symmetrical, with opposed convex surfaces defining generally spherical sections. The lens and the cornea cooperate to focus light on the retina. The retina in turn cooperates with the nerves and the brain, so that light impinging on the retina is perceived as an image.

The light refraction which takes place in the cornea and the lens translates into an optical correction of about 60 diopters, with the cornea accounting for about 40 diopters and the lens accounting for about 20 diopters. Other refracting structures also are present in the eye, but are disregarded to simplify the subject explanation.

A cataract is a condition where the normally clear lens of the eye becomes progressively opaque. This opacification typically occurs over an extended period of time, and the amount of light which passes through the lens decreases with increasing degrees of opacity. As the ability of the cataract lens to transmit light decreases, the ability of the eye to perceive images also decreases. Blindness ultimately can result. Since there are no known methods for eliminating the opacity of a cataract lens, it generally is necessary to surgically remove the opaque lens to permit the unobstracted passage of light through the pupil to the retina. The cataract lens is removed through a generally horizontal incision made at the superior part of the juncture where the cornea and the sclera meet. It is estimated that about 500,000 cataract lenses will be surgically removed in the United States during 1983.

Once the cataractous lens has been surgically removed, light can be readily transmitted through the pupil and toward the retina. However, as noted above, the lens of the eye performs a significant light focusing function. Consequently, with the lens removed, the optical system of the eye is left about 20 diopters "short", and light is no longer properly focused on the retina. Eyeglasses, contact lenses and intraocular lenses are the three types of optical aids that commonly may be employed after cataract surgery to refocus the light on the retina.

Eyeglasses include lenses which are spaced from the cornea of the eye. The air space between the lens and the cornea causes an image magnification of more than 7%. Unfortunately, the brain cannot assimilate this magnification, and as a result an object appears double. This is a particular problem if the individual had only one cataract eye. Eyeglasses also substantially limit peripheral vision.

Contact lenses rest directly on the cornea of the eye, thus eliminating the air space. As a result, there is a much smaller image magnification with contact lenses than there is with eyeglasses, and the brain typically can fuse the images perceived by an eye with a contact lens and one without. Contact lenses, however, are less than perfect. For example, contact lenses are quite fragile and can be easily displaced from their proper position on the cornea. Additionally, the lenses must be periodically replaced because of protein build-up on the surface of the lens which can cause conjunctivitis. Furthermore, many of the elderly people who require cataract operations do not have the required hand coordination to properly remove or insert the lens.

Intraocular lenses first became available as optical aids to replace removed cataract lenses in about 1955. These lenses are placed in the eye, and thus closely simulate the optics of the natural lens which they are replacing. Unlike eyeglasses, there is virtually no image distortion with a properly made and placed intraocular lens. Also, unlike contact lenses there is no protein build up on intraocular lenses and the lenses require no care by the patient. Even though intraocular lenses have come into use relatively recently, it is estimated that they will be used for optical correction in approximately 80% of the 500,000 cataract operations anticipated in the United States during 1983.

The prior art intraocular lens typically is either of plano-convex construction or double convex construction, with each curved surface defining a spherical section. The lens is placed in the eye through the same incision which is made to remove the cataract lens. As noted above, this incision typically is made along the superior part of the eye at the juncture of the cornea and the sclera. The recipient of an intraocular lens typically will have clear vision with normal peripheral vision if there is no astigmatism. However, in virtually all instances the surgery itself induces astigmatism. Postoperative induced astigmatism is attributable to the healing characteristics of the eye adjacent the incision through which the cataract lens is removed and the intraocular lens is inserted. More particularly, the sutured incision in the eye tends to heal more slowly and less completely as compared to incisions in the skin. For example, a sutured incision in skin typically heals in five to seven days, whereas a comparable incision in the eye may take eight weeks to a year to properly heal depending on the method of suturing. This slow healing rate typically is attributable to the nature of the eyes' tissue, poor vascularity and topical cortisone use after surgery. During the period when the eye is healing, the sutured area tends to spread and thus the prior spherical cornea is made other than spherical. Since the incision always is generally horizontally aligned, the spreading is always along the vertical meridian. Consequently, the optical system of the eye which previously had been spherical becomes "toric" with the vertical meridian of the optical system providing a different optical power than the horizontal meridian. This nonspherical configuration of the optic system is generally referred to as "astigmatism".

It now is known that the degree of this induced astigmatism varies according to the type of sutures used and the suturing technique and the technical skill and care employed by the surgeon. For example, the use of a fine nylon suturing material typically results in a smaller deviation from sphericity than the use of silk or absorbable sutures. Generally, the induced astigmatism varies from 0.5 to 5 diopters. Additionally, the astigmatism resulting from the operation is always in the vertical meridian. The induced astigmatism typically is corrected by prescription eyeglasses where the vertical meridian has more power than the horizontal meridian.

It now has been discovered that although the amount of induced astigmatism is subject to several variables, there is little variation in the astigmatism induced by each surgeon. Thus, a surgeon who continually uses the same type of suturing material in the same manner can predict with reasonable accuracy the amount of astigmatism that he or she will induce.

In view of the above, it is an object of the subject invention to provide an intraocular lens for eliminating or reducing astigmatism.

It is another object of the subject invention to provide an intraocular lens which eliminates or reduces the astigmatism induced by cataract surgery.

It is a further object of the subject invention to provide an intraocular lens of toric configuration.

It is an additional object of the subject invention to provide a precisely manufactured toric lens with the variation in meridians reflecting the astigmatism that the surgeon anticipates inducing.

It is still another object of the subject invention to provide a toric intraocular lens constructed to be properly and easily aligned when placed in the eye.

SUMMARY OF THE INVENTION

The subject invention is directed to an intraocular lens which is of toric configuration wherein at final placement within the eye the vertical meridian is optically less than the horizontal meridian. The difference between the optical strengths of vertical and horizontal meridians is specifically selected to reflect the eyes' prior to surgery astigmatism, suturing material and technique employed by an individual surgeon. More particularly, by selecting a lens having a vertical meridian which is weaker than the horizontal meridian, the postoperative stretching which occurs adjacent the incision in the eye can be offset. Since this postoperative astigmatism is always in the same direction, and can be predicted by each surgeon with reasonable accuracy, the final induced astigmatism can either be eliminated entirely or substantially reduced. The toric lens can be either plano-convex, double convex, or concave-convex and can be of either circular or non-circular configuration.

The intraocular lens typically is quite small, and the structural differences between the horizontal and vertical meridians is even smaller. As a result, it would be difficult for the surgeon to quickly and reliably determine which meridian should be aligned with the vertical. Therefore, it is preferred that the lens be manufactured with a structural characteristic which clearly identifies the vertical and/or horizontal meridian. For example, intraocular lenses include haptics or legs which extend from the perimeter of the lens outwardly to properly support the lens in the eye. If standardization implies identification of the vertical axis, on lenses having two haptics, the haptics preferably would be aligned along the vertical meridian. On lenses having more than two haptics, one of the haptics could be of different configuration or color to identify the vertical meridian. Alternatively, some other marking could be incorporated into the perimeter of the lens to indicate the vertical alignment.

DETAILED DESCRIPTION OF THE PREFERRED EMBODIMENTS

Figure 1:
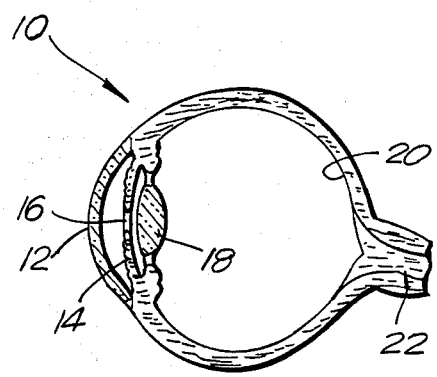
FIG. 1 is a cross-sectional side view of a human eye prior to removal of the lens.

With reference to FIG. 1, the normal human eye is identified generally by the numeral 10. The eye 10 includes a cornea 12, an iris 14, a pupil 16, a lens 18, a retina 20 and an optic nerve 22. In the normal eye, light is transmitted through the cornea 12, the pupil 16 and the lens 18 and is focused on the retina 20.

A cataract is by definition an opacification of the lens 18. Cataracts generally develop over time, thus gradually reducing the amount of light which reaches the retina 20.

Figure 2:
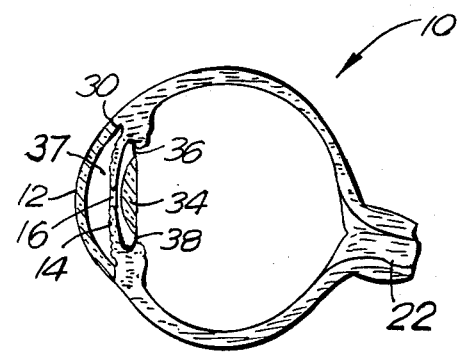
FIG. 2 is a cross-sectional side view of an eye after surgical removal of the lens and implantation of a new lens.
Figure 3:
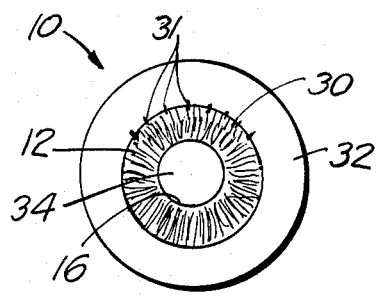
FIG. 3 is a front view of the eye shown in FIG. 2.

Cataracts generally are treated surgically by making an incision 30 at the point where the cornea 12 and sclera 32 meet, as shown in FIGS. 2 and 3, and removing the cataract lens 18. A new intraocular lens 34 then is inserted into the eye 10 to replace the light focusing functions which previously had been carried out by lens 18. As shown most clearly in FIG. 2, the intraocular lens 34 is inserted behind the iris 14. This type of lens is referred to as a posterior chamber lens, and is becoming the most commonly used type of intraocular lens. However, anterior chamber lenses, which are placed in area 37 intermediate the cornea 12 and iris 16, or iris plane lenses which are inserted into the area of the pupil 16 also are known. The lens of the subject invention can be manufactured for placement in any of these positions in the eye.

As noted above, the eye tissue heals very slowly. Thus, it may take eight weeks to one year for the incision 30 to properly heal. During this healing period, there is a tendency of the eye 10 to stretch and thus flatten in the vicinity of incision 30, such that the vertical meridian becomes optically different than the horizontal meridian. These differences between the focusing powers of the two meridians result in an astigmatism induced by the surgery. The degree of this induced astigmatism, as noted above, is reasonably predictable according to the type of sutures 31 used and the surgeon's technique.

Figure 4:
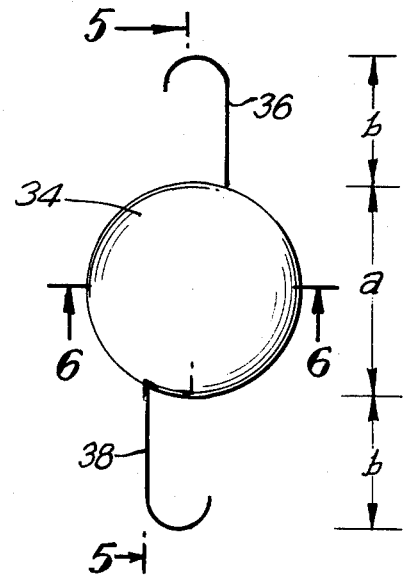
FIG. 4 is an elevational view of the toric lens of the subject invention.
Figure 5:
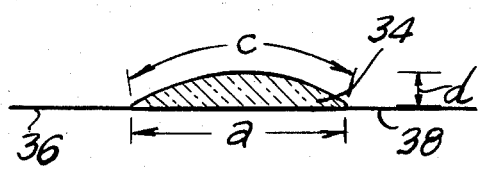
FIG. 5 is a cross-sectional view taken along lines 5—5 in FIG. 4.
Figure 6:
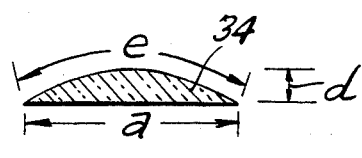
FIG. 6 is a cross-sectional view taken along lines 6—6 in FIG. 4.

The intraocular lens 34 of the subject invention, as shown in FIGS. 4–6, differs from the prior art intraocular lenses in that instead of defining a section of a sphere, the intraocular lens 34 defines a toric section. As shown in FIG. 4, the lens 34 is circular with a diameter of approximately 6 millimeters, as indicted by dimension "a". Haptics 36 and 38 function as legs which support the lens 34 in its proper position in the posterior chamber of the eye. Each haptic 36 and 38 extends approximately 4 milimeters from the lens 34 as indicated by dimension "b" in FIG. 4. Thus, the total length of the lens 34 and haptics 36 and 38 is approximately 14 millimeters.

The lens 34 is formed such that the vertical meridian as described by arc "c" as shown in FIG. 5 is optically weaker than the horizontal meridian described by arc "e" as shown in FIG. 6. Of course, however, the thickness of the lens 34 at its center as indicated by dimension "d", remains constant. Thus, the difference in the respective optical strengths of vertical and horizontal meridians "c" and "e" reflects different structural contours in the vertical and horizontal meridians "c" and "e", which in turn, results in different light refracting characteristics. By properly orienting lens 34 in the eye 10, the optical differences in the vertical and horizontal meridians "c" and "e" can effectively offset the astigmatism induced by the surgery. More particularly, the surgeon can select a lens having a vertical meridian strength which is weaker than the horizontal meridian strength by an amount calculated to offset the astigmatism which his or her surgical hand typically induces. Additionally, it should be noted that some patients have a pre-existing astigmatism. This condition, of course, should be accounted for in determining the relative strengths of the meridians of lens 34.

To ensure that the lens 34 is properly aligned in the eye 10, the haptics 36 and 38 are positioned in line with the vertical meridian. Thus by vertically aligning the haptics 36 and 38, the surgeon is assured that the weaker vertical meridian of the lens 34 is aligned to offset the astigmatism that will be induced by the surgery. It is recognized that some surgeons will intentionally rotate lens 34 so that the haptics 36 and 38 are aligned horizontally. These surgeons would have to clearly specify the respective meridian strengths with reference to their preferred haptic alignment when ordering lenses.

As an example, if a surgeon knew that in most instances he induced two diopters of post-surgery astigmatism in the verical meridian, he would select an intraocular lens with two diopters less power in the vertical plane. Thus, in that surgeon's typical operation, the two diopters of toricity in the intraocular lens would offset the two diopters of astigmatism, and the result would be spherical postoperative vision.

With reference to the same example, assume that the surgeon averages 2.0 diopters of induced astigmatism, but actually may vary within plus or minus 25% of that average in any particular operation. Thus, if the induced astigmatism is 25% less than anticipated, there would only be 1.5 diopters of astigmatism induced by the surgery. Since the surgeon would be unable to predict the variation from his average induced astigmatism prior to surgery, he would already have implanted his standard intraocular lens with two diopters less power in the vertical plane. Consequently, even with the toric lens there would be 0.5 diopters of postoperative astigmatism. Although this is less than desirable it can easily be corrected by eyeglasses, and is substantially better than the astigmatism that would have resulted had a spherical lens been used.

If the surgeon had varied from his average 25% in the opposite direction, and had actually induced an astigmatism of 2.5 diopters, the implanted toric lens would not quite offset the induced astigmatism, and there would be a resultant 0.5 diopters of postoperative astigmatism. As noted previously, this magnitude of astigmatism readily can be corrected with eyeglasses and the patient would be much better off than if a spherical lens had been used.

In summary, an improved intraocular lens is provided to eliminate or reduce the postoperative astigmatism that is induced during eye surgery, such as surgery to replace cataract lenses with intraocular lenses. The invention takes advantage of the facts that the postoperative induced astigmatism always is along the vertical meridian and that each surgeon can reasonably predict the degree of astigmatism which he or she is likely to induce. To take advantage of these facts, the subject invention is directed to a lens of toric configuration rather than the typical intraocular lens having spherical refracting surfaces. More particularly, the subject invention is directed to a lens finally placed within the eye having a vertical meridian which is optically weaker than the horizontal meridian by an amount sufficient to offset the average astigmatism induced by the particular surgeon. To ensure that the subject toric intraocular lens is properly inserted, the lens is appropriately marked to identify the vertical meridian. Preferably this marking of the vertical meridian is provided by the alignment, configuration, and/or color of the haptics.

While the preferred embodiment of the subject invention has been described and illustrated, it is obvious that various changes and modifications can be made therein without departing from the spirit of the present invention which should be limited only be the scope of the appended claims. More particularly, the preceding detailed description shows a circular plano-convex intraocular lens having two haptics. The invention however covers double convex intraocular lenses, convex-concave intraocular lenses, non-circular intraocular lenses, and intraocular lenses having either more or fewer than two haptics.

What is claimed is:

1. A method for offsetting postoperative astigmatism induced by a surgeon as a result of cataract surgery, wherein the surgeon has estimated the induced astigmatism based on previous cataract surgery performed by said surgeon, said method comprising the steps of:

making an incision at the upper part of the juncture between the cornea and the sclera;

removing the cataract lens;

providing a toric lens having two transverse meridians of unequal power, with the difference in power being sufficient to offset the astigmatism anticipated to be induced by the surgery;

inserting the lens in the eye such that the weaker power meridian is vertically aligned; and suturing the incision in the eye, whereby the toric lens offsets the astigmatism induced by the surgery.

2. A method as claim 1 wherein the lens is placed in the posterior chamber of the eye.

3. A method as in claim 1 wherein the lens is placed in the anterior chamber of the eye.

* * * * *